United States Patent [19]

Boyd

[11] Patent Number: 4,882,576
[45] Date of Patent: Nov. 21, 1989

[54] REMOTE COMBUSTIBLE GAS SENSOR

[76] Inventor: Monty Boyd, Rte. #2, Box 652, Muldrow, Okla. 74948

[21] Appl. No.: 154,101

[22] Filed: Feb. 9, 1988

Related U.S. Application Data

[63] Continuation-in-part of Ser. No. 934,794, Nov. 25, 1986, abandoned.

[51] Int. Cl.⁴ ............................................. G08B 17/10
[52] U.S. Cl. ..................................... 340/632; 73/1 G; 73/1 R; 422/83; 422/98
[58] Field of Search ......................... 73/1 G, 23, 1 R; 340/632–634; 422/83, 86, 94, 98; 204/406, 409

[56] References Cited

U.S. PATENT DOCUMENTS 4,384,925  5/1983  Stetter et al. ......................... 73/1 G
4,590,789  5/1986  Kunze .................................. 73/1 G
4,630,038 12/1986  Jordan ................................. 73/1 G Primary Examiner—Donald J. Yusko
Assistant Examiner—Tyrone Queen
Attorney, Agent, or Firm—George A. Bode; D. Neil LaHaye

[57] ABSTRACT

A combustible gas sensor with a calibration test adaptor. A standard combustible gas sensor attached to a transmitter in transmitter housing has a body portion attached thereto which is adapted to receive and slowly distribute test gas in the vicinity of the combustible gas sensor. A flexible bladder fastened to the main body portion receives the test gas, inflates, and slowly releases the test gas through a sintered stainless steel plug mounted in one end of the flexible bladder.

16 Claims, 3 Drawing Sheets

REMOTE COMBUSTIBLE GAS SENSOR

This application is a continuation-in-part application of a previous application by the same inventor bearing U.S. Ser. No. 06/934,794 filed Nov. 25, 1986 now abandoned. The entire previous application Ser. No. 934,794 is incorporated herein by reference as if set forth in full below.

BACKGROUND OF THE INVENTION

1. Field of the Invention

The present invention relates to combustible gas detectors or sensors and in particular to calibration means for combustible gas sensors.

2. General Background

A variety of industrial operations such as pulp mills, refineries, sewerage and waste water plants and the oil and gas industry constantly face the risk of the presence or production of combustible gases such as hydrocarbons. As an aid to increase safety in such areas, sensors have been developed which are sensitive to the presence of such gases. Upon sensing a pre-set level of the gas being monitored, the sensor provides an electric signal which sets off an alarm system to warn personnel of the unsafe condition. However, these sensors must be exposed to the gas on a regular basis to ensure that the sensor is properly calibrated. This helps prevent annoying and costly false alarms and failure to alarm when the gas reaches a dangerous level. However, this calibration operation has involved the necessary use of scaffolding or ladders to reach sensors located in remote locations which are difficult to reach or hazardous. The known art has presented a variety of approaches to the situation.

U.S. Pat. No. 4,305,724 entitled "Combustible Gas Detection System" discloses the use of an active sensor maintained at a controlled temperature in respect of a reference sensor and which measures combustible gases by means of a bridge-sampling system and a variable duty cycle system.

U.S Pat. No. 4,476,706 entitled "Remote Calibration System" discloses calibration of combustible gas detectors by signals applied to a sealed, explosion-proof sensor assembly to effect a remote calibration sequence.

Japanese Pat. No. JA57-128840 discloses a calibration device having a gas ported pressure sensor.

U.S. Pat. Nos. 4,555,930 entitled "Digital Gas Sensing System," 4,279,142 entitled "Technique For In Situ Calibration Of A Gas Detector," No. 4,534,204 entitled "Calibration Method For Ultra Sensitive Noble Gas Leak Detector," No. 4,553,423 entitled "Gas Doser," No. 4,124,475 entitled "Hydrogen Sulfide Monitoring System," No. 4,260,950 entitled "Automatic Portable PH Meter And Method With Calibration Receptacle," No. 4,432,224 entitled "Hydrogen Sulfide Measuring Systems And The Like," and No. 4,489,590 entitled "Method And Appartus For Gas Detector Calibration" all disclose combustible gas detection systems which are representative of the art.

Although a variety of systems are shown in the art, none these systems provide a means for calibrating systems through the use of calibration ports which do not require the complete replacement of the expensive sensors and housings. Replacing and discarding of entire sensors and housings is ineffecent and expensive. Thus, there exists a need for providing means for calibrating sensors without the necessity of replacing the entire sensor and housing.

SUMMARY OF THE PRESENT INVENTION

The present invention solves the aforementioned problems in a straightforward manner. What is provided is a combustible gas sensor with a calibration test adaptor. A standard combustible gas detector sensor such as that normally used and attached to the transmitter housing assembly is adapted to receive the gas being monitored during calibration operations from a remote location. The dust cover normally present on the sensor is removed and replaced by the present invention which is comprised of a main body portion adapted to be easily fastened to the sensor. The main body portion is provided with a calibration gas port adapted to receive test gas through standard tubing or piping from a remote location. An interchangeable bladder attached to the port and body is inflated by the gas and slowly releases the gas for calibration purposes.

In view of the above, it is an object of the present invention to provide a remote combustible gas sensor that prevents the interference of wind and other factors from creating an inacurate calibration.

It is another object of the present invention to provide a remote combustible gas sensor that presents no restriction or impairment to normal diffusion sensing in the event of accidental release of the gas.

It is yet another object of the present invention to provide a remote combustible gas sensor that in the event of malfunction will fail in a mode which will allow normal detector operation.

BRIEF DESCRIPTION OF THE DRAWINGS

For a further understanding of the nature and objects of the present invention, reference should be had to the following description, taken in conjunction with the accompanying drawings in which like parts are given like reference numerals and, wherein.

DETAILED DESCRIPTION OF THE PREFERRED EMBODIMENT

Figure 1:
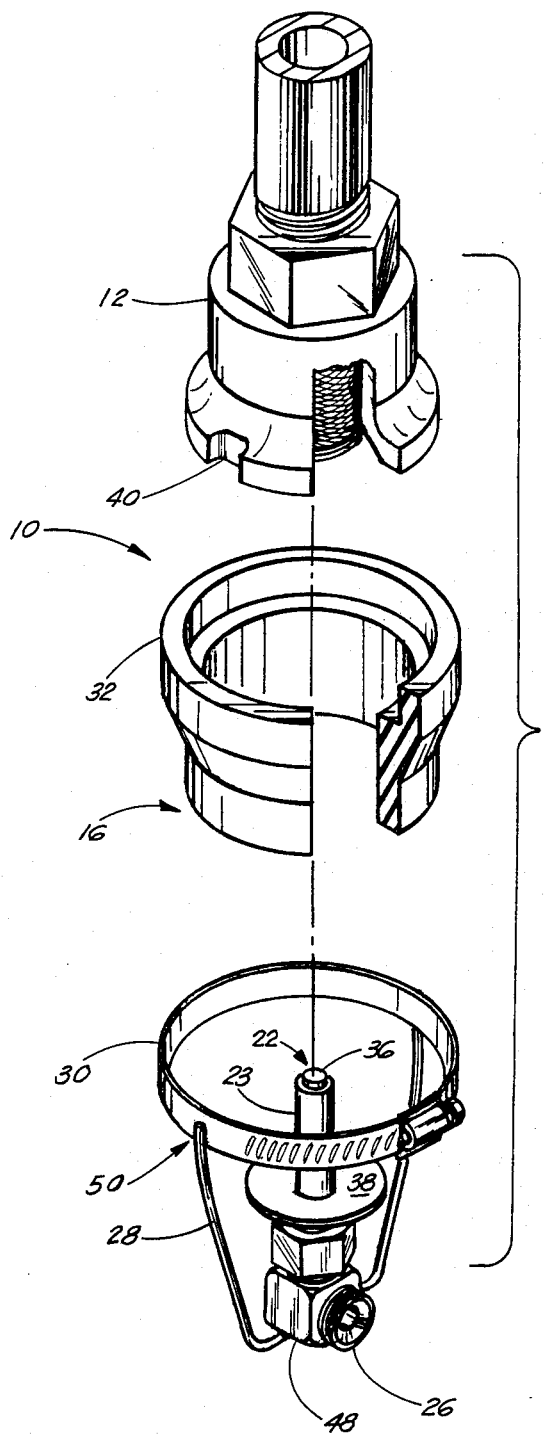
FIG. 1 is an exploded view of the preferred embodiment of the apparatus of the present invention.
Figure 2:
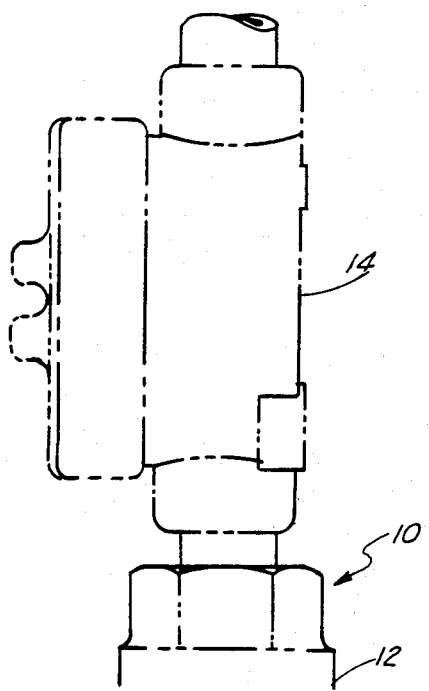
FIG. 2 is a partial side sectional view of the apparatus of FIG. 1.

Referring to the drawings, it is seen in FIGS. 1 and 2 that the invention is generally referred to by the numeral 10. Remote combustible gas sensor 10 is generally comprised of combustible gas sensor 12, transmitter housing 14, and calibration test adaptor 16.

Combustible gas sensor 12 may be of any conventional, type used in industrial applications such as that manufactured by Delphian for detecting combustible gases such a hydrocarbons. Upon detection of a predetermined level of the combustible gas, a signal from sensor 12 is directed by a transmitter (not shown) in transmitter housing 14, connected to sensor 12, to an alarm (not shown) via wiring harness 15 to warn the operator of dangerous gas levels.

Attached to combustible gas sensor 12 is calibration test adaptor 16. Calibration test adaptor 16 is generally comprised of main body portion 48, means 50 for mounting body portion 48 to sensor 12, and test gas distribution means 22 mounted on body portion 48.

As best seen in FIGS. 1-3 and 5, main body portion 48 is provided with bore 24 therethrough to direct gas to gas distribution means 22. Distribution means 22 is comprised of bladder 23 and steel plug 36 to be discussed further herein. Main body portion 48 is adapted to receive test gas from a source or gas supply 20 via delivery tubing 18 by being provided with thread fitting 26. In the preferred embodiment, threaded fitting 26 is sized such that it is easily attached to standard one-quarter (¼") inch steel tubing. The test gas is then delivered from source 20 through steel tubing 18 in fluid communication with main body portion 48 and through bore 24 to gas distribution means 22.

Figure 3:
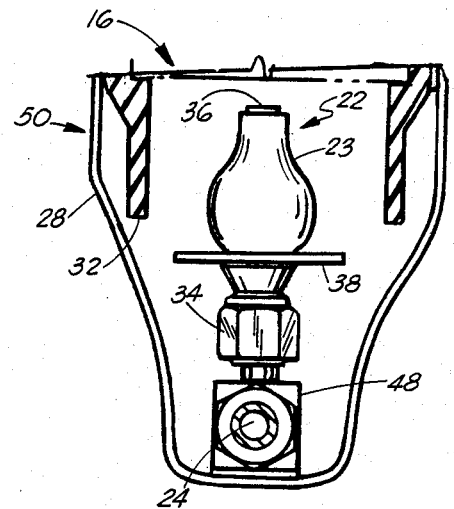
FIG. 3 is a side sectional view of the main body portion of the apparatus of FIG. 1 as the test gas begins to inflate the interchangeable bladder.
Figure 5:
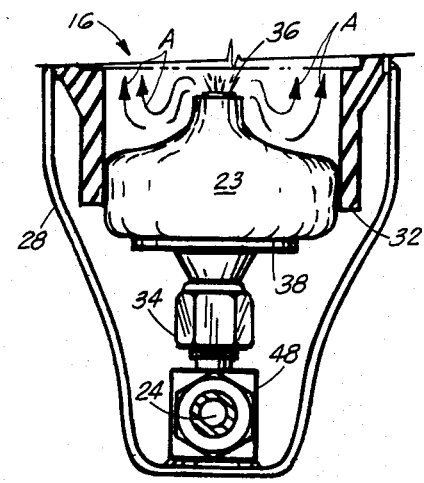
Figure 4:
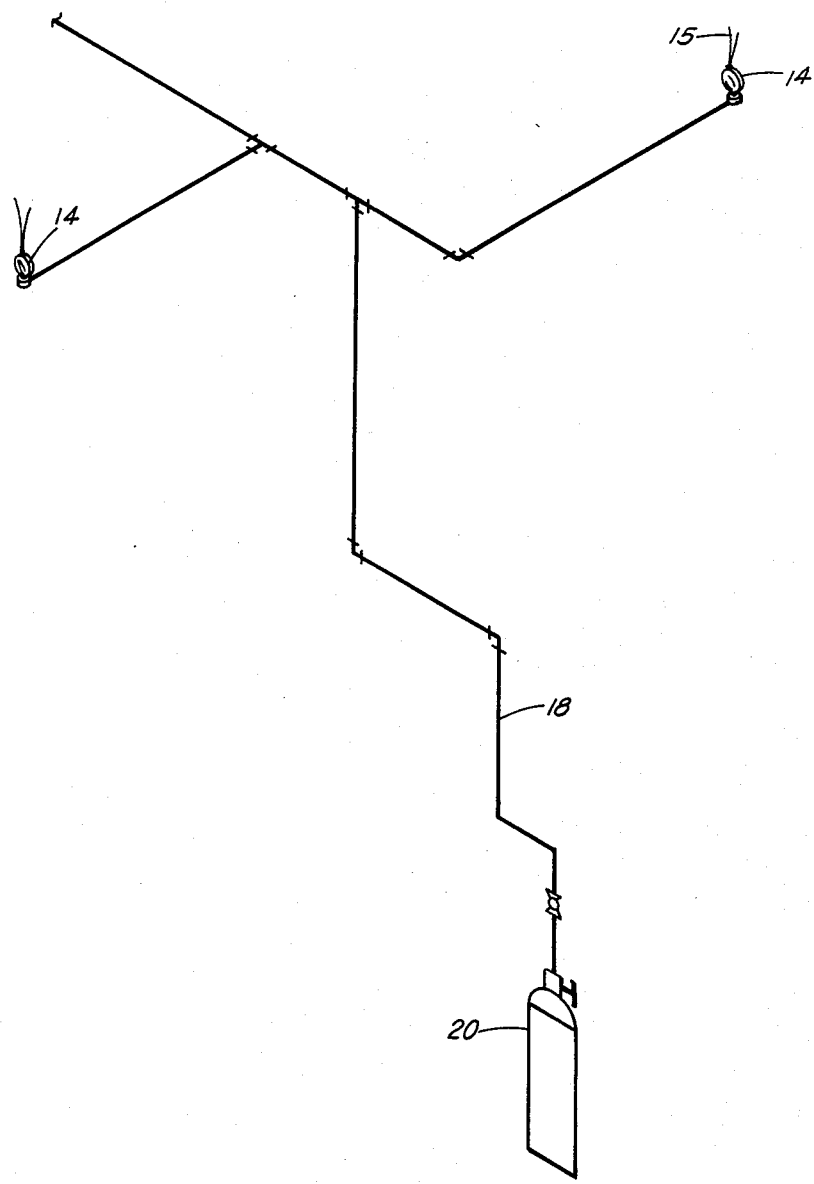
FIG. 4 is a schematic illustration of the preferred embodiment of the present invention installed in an operational system (and is identical to FIG. 4 of the parent application Ser. No. 934,794 filed Nov. 25, 1986 incorporated herein by reference); and, FIG. 5 is a partial side sectional view of the main body portion of the apparatus of FIG. 1 with the interchangeable bladder inflated and releasing the test gas.

Means 50 for mounting body portion 48 to combustible gas sensor 12 is comprised of generally U-shaped frame member 28 and clamp 30. As best seen in FIGS. 2, 3 and 5, frame member 28 is attached across one end of body portion 48 opposite gas distribution means 22 and extends around body portion 48. Clamp 30, which may be of any conventional suitable type, is attached between the two legs of frame member 28. Cup 32 is annularly shaped, open at both ends, and sized to fit within mounting means 50 and around combustible gas sensor 12. Clamp 30 is tightened around cup 32 whereby it serves as a part of mounting means 20. Cup 32 also serves a second purpose—as means for temporarily containing the test gas within the immediate vicinity of sensor 12 to prevent air movement from disbursing the test gas which would result in inacurate calibration results.

Test gas received by main body portion 48 flows through bore 24 when received at fitting 26 and thus through body portion 48 to test gas distribution means 22 which is adapted to slowly release the test gas within cup 32. Test gas distribution means 22 is preferably formed from a flexible and inflatable bladder 23 mounted on body portion 48 by means of mounting nut 34. Bladder 23 is provided with plug 36 which is a means for slowly releasing the test gas to obtain an acurate calibration of combustible gas sensor 12. Means 36 is formed from "sintered" stainless steel in the preferred embodiment as this form of stainless steel is porous and allows the slow diffusion of gas therethrough. Thus, the sintered stainless steel is inserted in one end of bladder 23 as plug 36.

As best seen in FIGS. 3 and 5, means 38 for restricting the expansion of bladder 23 is provided adjacent the lower end thereof. In the preferred embodiment, restricting means 38 takes the form of a washer which fits snugly around bladder 23 so as to prevent excess stress on the bladder at the end where it connects with nut 34 by limiting the inflatability of the lower end of bladder 23. This contributes to increased life expectancy of the bladder. Naturally, washer 38 has a sufficient thickness so as not to cut into bladder 23 as the bladder is inflated.

In set up and operation, after the dust cover (not shown), if any, has been removed from combustible gas sensor 12, which is connected to transmitter housing 14 and the transmitter contained therein, calibration test adapter 16 is attached to sensor 12 by means of frame 28, clamp 30, and cup 32. A test gas supply line or delivery tubing 18 is attached to threaded fitting 26 on main body portion 48. Test gas delivered from source 20 flows through body portion 48 by way of tubing 18 and bore 24 into gas distribution means 22 attached to body portion 48. Bladder 23 of gas distribution means 22 is caused to inflate by the pressurized gas and is maintained within cup 32 as best seen in FIG. 5. Restriction means 38 also prevents excessive stress on bladder 23 at nut 34. Means 36 for slowly releasing the test gas, is preferably comprised of a sintered stainless steel plug inserted at one end of bladder 23, which releases gas from within cup 32. The gas then activates sensor 12 which sends a signal to the transmitter in housing 14. The operator then reads the signal to check that sensor 12 is properly calibrated.

As seen in FIG. 1, sensor 12 is provided with at least one bayonet slot 40 in the area where it is fastened to cup 32. This serves as a means for allowing the test gas to slowly escape without being adversely affected by air movement in the vicinity of the device. It can be seen that one advantage of remote combustible gas sensor 10 is that it is failsafe. Since there are no mechanical moving parts, in the event the unit does fail, it will fail in a mode which allows normal detector operation.

Because many varying and differing embodiments may be made within the scope of the inventive concept herein taught, and because many modifications may be made in the embodiment herein detailed in accordance with the descriptive requirement of the law, it is to be understood that the details herein are to be interpreted as illustrative and not in a limiting sense.

What is claimed as invention is:

1. A remote combustible gas sensor and calibrator therefor, comprising:
   a. a combustible gas sensor;
   b. a transmitter housing connected to said combustible gas sensor for transmitting signals indicating a predetermined level of combustible gas; and
   c. a calibration means attached to said combustible gas sensor, said calibration means comprising:
      i. a main body portion;
      ii. means attached to said main body portion for mounting said calibration means on said combustible gas sensor;
      iii. means on said main body portion for receiving test gas; and
      iv. test gas distribution means mounted on said main body portion, including a flexible bladder attached to said main body portion.

2. The remote sensor and calibrator of claim 1, wherein said mounting means comprises:
   a. a frame attached to said main body portion; and
   b. a clamp attached to said frame.

3. The remote sensor and calibrator of claim 1, wherein said means for receiving test gas comprises said main body portion having a bore therethrough.

4. The remote sensor and calibrator of claim 1, further comprising means mounted in said flexible bladder for slowly releasing test gas from said bladder.

5. The remote sensor of claim 4, wherein said release means comprises a sintered stainless steel plug.

6. The remote sensor and calibrator of claim 1, further comprising restricting means for limiting the inflation of said bladder.

7. The remote sensor and calibrator of claim 1, further comprising means for temporarily containing the test gas within the vicinity of said combustible gas sensor.

8. A remote combustible gas sensor, comprising:
  a. a combustible gas sensor;
  b. a transmitter housing connected to said combustible gas sensor for transmitting signals indicating a predetermined level of combustible gas;
  c. a calibration test adaptor having a main body portion attached to said combustible gas sensor; and,
  d. means provided on said main body portion for receiving and distributing test gas, further comprising:
    i. said main body portion having a bore therethrough; and,
    ii. a flexible bladder attached to said main body portion and in communication with said bore.

9. The remote sensor of claim 8, further comprising means for temporarily containing the test gas within the vicinity of said combustible gas sensor.

10. The remote sensor of claim 8, further comprising means mounted on said bladder for slowly releasing test gas from said bladder.

11. The remote sensor of claim 10, wherein said release means comprises a sintered stainless steel plug.

12. The remote sensor of claim 8, further comprising restricting means for limiting the inflation of said bladder.

13. A remote combustible gas sensor, comprising:
  a. a combustible gas sensor;
  b. a transmitter housing connected to said combustible gas sensor for transmitting signals indicating a predetermined level of combustible gas;
  c. a calibration test adaptor having a main body portion attached to said combustible gas sensor;
  d. said main body portion having a bore therethrough;
  e. a flexible bladder mounted on said main body portion and in communication with said bore for receiving and distributing test gas; and
  f. means mounted between said combustible gas sensor and said main body portion for temporarily containing the test gas within the vicinity of said combustible gas sensor.

14. The remote sensor of claim 13, further comprising a washer positioned around the lower end of said bladder whereby inflation of said bladder is restricted at its lower end.

15. The remote sensor of claim 13, further comprising a sintered stainless steel plug positioned in one end of said bladder.

16. The remote sensor of claim 13, wherein said test gas containment means comprises an annular shaped cup open at each end.

* * * * *